(12) United States Patent
Barthe et al.

(10) Patent No.: US 8,708,935 B2
(45) Date of Patent: *Apr. 29, 2014

(54) SYSTEM AND METHOD FOR VARIABLE DEPTH ULTRASOUND TREATMENT

(75) Inventors: Peter G. Barthe, Phoenix, AZ (US); Michael H. Slayton, Tempe, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,754

(22) Filed: Jul. 12, 2010

(65) Prior Publication Data

US 2010/0280420 A1    Nov. 4, 2010

Related U.S. Application Data

(63) Continuation of application No. 10/944,500, filed on Sep. 16, 2004, now Pat. No. 7,824,348.

(51) Int. Cl.
*A61H 7/00* (2006.01)

(52) U.S. Cl.
USPC .............. 601/2; 601/3; 600/437; 600/439; 600/443; 600/446; 600/459

(58) Field of Classification Search
USPC .......... 600/437, 439, 443, 446, 459; 601/2–4
See application file for complete search history.

(56) References Cited

U.S. PATENT DOCUMENTS

| | | |
|---|---|---|
| 2,427,348 A | 9/1947 | Bond et al. |
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |

(Continued)

FOREIGN PATENT DOCUMENTS

| | | |
|---|---|---|
| DE | 4029175 | 3/1992 |
| DE | 10140064 | 3/2003 |

(Continued)

OTHER PUBLICATIONS

Chen, L. et al., ""Effect of Blood Perfusion on the ablation of liver perenchyma with high intensity focused ultrasound,"" Phys. Med. Biol; 38:1661-1673; 1993b.

Damianou et al., Application of the Thermal Dose Concept for Predicting the Necrosed Tissue Volume During Ultrasound Surgery, 1993 IEEE Ultrasound Symposium, pp. 1199-1202.

(Continued)

*Primary Examiner* — Baisakhi Roy
(74) *Attorney, Agent, or Firm* — Michael J. Lang

(57) ABSTRACT

A non-invasive variable depth ultrasound treatment method and system comprises a variable depth transducer system configured for providing ultrasound treatment to a patient. An exemplary variable depth transducer system can comprise a transducer configured to provide treatment to more than one region of interest, such as between a deep treatment region of interest and a superficial region of interest, and/or a subcutaneous region of interest. The variable depth transducer can comprise a transduction element having a piezoelectrically active layer, matching layers and/or other materials for generating radiation or acoustical energy. The variable depth transducer may be configured to operate at moderate frequencies within the range from approximately 750 kHz to 20 MHz or more. In addition, the transduction element may be configured with a variable depth device comprising one or more materials configured to allow for control and focusing/defocusing of the acoustic energy to more than one region of interest.

29 Claims, 9 Drawing Sheets

(56) References Cited

U.S. PATENT DOCUMENTS

| | | |
|---|---|---|
| 4,101,795 A | 7/1978 | Fukumoto |
| 4,213,344 A | 7/1980 | Rose |
| 4,276,491 A | 6/1981 | Daniel |
| 4,315,514 A | 2/1982 | Drewes et al. |
| 4,325,381 A * | 4/1982 | Glenn ........................... 600/446 |
| 4,343,301 A | 8/1982 | Indech |
| 4,372,296 A | 2/1983 | Fahim |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,441,486 A | 4/1984 | Pounds |
| 4,452,084 A | 6/1984 | Taenzer |
| 4,484,569 A | 11/1984 | Driller |
| 4,513,749 A | 4/1985 | Kino |
| 4,527,550 A | 7/1985 | Ruggera et al. |
| 4,528,979 A | 7/1985 | Marchenko |
| 4,567,895 A | 2/1986 | Putzke |
| 4,586,512 A | 5/1986 | Do-Huu |
| 4,601,296 A | 7/1986 | Yerushalmi |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose et al. |
| 4,917,096 A | 4/1990 | Englehart |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,973,096 A | 11/1990 | Joyce |
| 4,976,709 A | 12/1990 | Sand |
| 4,979,501 A | 12/1990 | Valchanov |
| 5,012,797 A | 5/1991 | Liang |
| 5,036,855 A | 8/1991 | Fry |
| 5,054,310 A * | 10/1991 | Flynn ........................... 73/1.86 |
| 5,054,470 A | 10/1991 | Fry |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki |
| 5,158,536 A | 10/1992 | Sekins |
| 5,163,421 A | 11/1992 | Bernstein |
| 5,178,135 A | 1/1993 | Uchiyama et al. |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger |
| 5,371,483 A | 12/1994 | Bhardwaj |
| 5,379,773 A | 1/1995 | Hornsby |
| 5,380,280 A | 1/1995 | Peterson |
| 5,383,917 A | 1/1995 | Desai et al. |
| 5,391,140 A | 2/1995 | Schaetzle |
| 5,391,197 A | 2/1995 | Burdette et al. |
| 5,406,503 A | 4/1995 | Williams, Jr. et al. |
| 5,419,327 A | 5/1995 | Rohwedder |
| 5,435,311 A | 7/1995 | Umemura |
| 5,458,596 A | 10/1995 | Lax |
| 5,460,595 A | 10/1995 | Hall et al. |
| 5,471,988 A | 12/1995 | Fujio et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,320 A | 4/1996 | Webster et al. |
| 5,507,790 A | 4/1996 | Weiss |
| 5,520,188 A * | 5/1996 | Hennige et al. ........... 600/459 |
| 5,522,869 A | 6/1996 | Burdette |
| 5,523,058 A * | 6/1996 | Umemura et al. ........... 422/128 |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,638,819 A | 6/1997 | Manwaring et al. |
| 5,647,373 A | 7/1997 | Paltieli |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,665,053 A | 9/1997 | Jacobs |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,769,790 A | 6/1998 | Watkins |
| 5,795,297 A | 8/1998 | Daigle |
| 5,795,311 A | 8/1998 | Wess |
| 5,810,888 A | 9/1998 | Fenn |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |

(56) References Cited

U.S. PATENT DOCUMENTS

| | | |
|---|---|---|
| 5,839,751 A | 11/1998 | Lutz |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,879,303 A | 3/1999 | Averkiou et al. |
| 5,882,557 A | 3/1999 | Hayakawa |
| 5,891,034 A | 4/1999 | Bucholz |
| 5,904,659 A | 5/1999 | Duarte |
| 5,919,219 A | 7/1999 | Knowlton |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,967,980 A | 10/1999 | Ferre et al. |
| 5,968,034 A | 10/1999 | Fulmer |
| 5,971,949 A | 10/1999 | Levin |
| 5,984,882 A | 11/1999 | Rosenschein |
| 5,997,471 A | 12/1999 | Gumb et al. |
| 5,997,497 A | 12/1999 | Nita et al. |
| 6,004,262 A | 12/1999 | Putz et al. |
| 6,007,499 A | 12/1999 | Martin et al. |
| 6,022,327 A | 2/2000 | Chang |
| 6,036,646 A | 3/2000 | Barthe |
| 6,039,048 A | 3/2000 | Silberg |
| 6,042,556 A * | 3/2000 | Beach et al. ............ 601/3 |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenschein |
| 6,113,559 A | 9/2000 | Klopotek |
| 6,120,452 A | 9/2000 | Barthe |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias et al. |
| 6,190,336 B1 | 2/2001 | Duarte et al. |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 * | 6/2001 | Averkiou et al. ......... 600/447 |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,311,090 B1 | 10/2001 | Knowlton |
| 6,315,741 B1 * | 11/2001 | Martin et al. ............ 601/3 |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,253 B1 | 7/2002 | Koop |
| 6,413,254 B1 | 7/2002 | Hissong |
| 6,419,648 B1 | 7/2002 | Vitek |
| 6,425,865 B1 | 7/2002 | Salcudean |
| 6,425,867 B1 | 7/2002 | Veazy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,491,657 B2 | 12/2002 | Rowe |
| 6,500,121 B1 | 12/2002 | Slayton |
| 6,500,141 B1 | 12/2002 | Irion |
| 6,508,774 B1 | 1/2003 | Acker |
| 6,511,428 B1 | 1/2003 | Azuma |
| 6,514,244 B2 | 2/2003 | Pope |
| 6,524,250 B1 | 2/2003 | Weber |
| 6,540,679 B2 | 4/2003 | Slayton |
| 6,540,685 B1 | 4/2003 | Rhoads et al. |
| 6,554,771 B1 | 4/2003 | Buil et al. |
| 6,569,099 B1 | 5/2003 | Babaev |
| 6,595,934 B1 | 7/2003 | Hissong |
| 6,599,256 B1 | 7/2003 | Acker |
| 6,607,498 B2 | 8/2003 | Eshel |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin et al. |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,719,449 B1 | 4/2004 | Laugharn, Jr. et al. |
| 6,719,694 B2 | 4/2004 | Weng |
| 6,749,624 B2 | 6/2004 | Knowlton |
| 6,775,404 B1 | 8/2004 | Pagoulatos et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna et al. |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |

(56) References Cited

U.S. PATENT DOCUMENTS

| | | |
|---|---|---|
| 6,932,771 B2 | 8/2005 | Whitmore |
| 6,936,044 B2 | 8/2005 | McDaniel |
| 6,936,046 B2 | 8/2005 | Hissong |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 * | 6/2006 | Weng et al. .................. 600/439 |
| 7,070,565 B2 | 7/2006 | Vaezy et al. |
| 7,074,218 B2 | 7/2006 | Washington et al. |
| 7,094,252 B2 | 8/2006 | Koop |
| 7,115,123 B2 | 10/2006 | Knowlton |
| 7,142,905 B2 | 11/2006 | Slayton |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,297,117 B2 * | 11/2007 | Trucco et al. .................. 600/443 |
| 7,347,855 B2 | 3/2008 | Eshel |
| RE40,403 E | 6/2008 | Cho et al. |
| 7,393,325 B2 | 7/2008 | Barthe |
| 7,491,171 B2 | 2/2009 | Barthe et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,758,524 B2 | 7/2010 | Barthe |
| 7,824,348 B2 * | 11/2010 | Barthe et al. .................. 601/3 |
| 7,955,281 B2 | 6/2011 | Pedersen et al. |
| 7,967,764 B2 | 6/2011 | Lidgren et al. |
| 8,057,389 B2 | 11/2011 | Barthe et al. |
| 8,128,618 B2 | 3/2012 | Gliklich et al. |
| 8,166,332 B2 | 4/2012 | Barthe et al. |
| 8,282,554 B2 | 10/2012 | Makin et al. |
| 2001/0009997 A1 | 7/2001 | Pope |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0082528 A1 | 6/2002 | Friedman et al. |
| 2002/0082589 A1 | 6/2002 | Friedman et al. |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193831 A1 | 12/2002 | Smith |
| 2003/0014039 A1 | 1/2003 | Barzell et al. |
| 2003/0018255 A1 * | 1/2003 | Martin et al. .................. 600/437 |
| 2003/0028113 A1 | 2/2003 | Gilbert et al. |
| 2003/0032900 A1 | 2/2003 | Ella |
| 2003/0036706 A1 * | 2/2003 | Slayton et al. .................. 600/439 |
| 2003/0040739 A1 | 2/2003 | Koop |
| 2003/0050678 A1 | 3/2003 | Sierra |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0097071 A1 | 5/2003 | Halmann et al. |
| 2003/0125629 A1 * | 7/2003 | Ustuner .................. 600/459 |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041880 A1 | 3/2004 | Ikeda et al. |
| 2004/0059266 A1 | 3/2004 | Fry |
| 2004/0073079 A1 | 4/2004 | Altshuler et al. |
| 2004/0073113 A1 | 4/2004 | Salgo |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington |
| 2005/0033201 A1 | 2/2005 | Takahashi |
| 2005/0055073 A1 | 3/2005 | Weber |
| 2005/0070961 A1 * | 3/2005 | Maki et al. .................. 607/2 |
| 2005/0074407 A1 | 4/2005 | Smith |
| 2005/0080469 A1 | 4/2005 | Larson |
| 2005/0113689 A1 | 5/2005 | Gritzky |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0228281 A1 | 10/2005 | Nefos |
| 2005/0240170 A1 | 10/2005 | Zhang et al. |
| 2005/0256406 A1 | 11/2005 | Barthe |
| 2005/0261584 A1 | 11/2005 | Eshel |
| 2005/0267454 A1 | 12/2005 | Hissong |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |

(56) References Cited

U.S. PATENT DOCUMENTS

| | | |
|---|---|---|
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0250046 A1 | 11/2006 | Koizumi et al. |
| 2006/0261584 A1 | 11/2006 | Blackburn |
| 2006/0282691 A1 | 12/2006 | Barthe |
| 2006/0291710 A1 | 12/2006 | Wang et al. |
| 2007/0032784 A1 | 2/2007 | Gliklich |
| 2007/0035201 A1 | 2/2007 | Desilets |
| 2007/0055154 A1 | 3/2007 | Torbati |
| 2007/0055156 A1 | 3/2007 | Desilets |
| 2007/0087060 A1 | 4/2007 | Dietrich |
| 2007/0088346 A1 | 4/2007 | Mirizzi et al. |
| 2007/0161902 A1 | 7/2007 | Dan |
| 2007/0167709 A1 | 7/2007 | Slayton |
| 2007/0208253 A1 | 9/2007 | Slayton |
| 2007/0239075 A1 | 10/2007 | Rosenberg et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pederson |
| 2008/0167556 A1 | 7/2008 | Thompson et al. |
| 2008/0200813 A1 | 8/2008 | Quistgaard |
| 2008/0214966 A1 | 9/2008 | Slayton |
| 2008/0221491 A1 | 9/2008 | Slayton |
| 2008/0275342 A1 | 11/2008 | Barthe |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain et al. |
| 2009/0069677 A1 | 3/2009 | Chen et al. |
| 2009/0182231 A1 | 7/2009 | Barthe et al. |
| 2009/0216159 A1 | 8/2009 | Slayton et al. |
| 2009/0253988 A1 | 10/2009 | Slayton et al. |
| 2009/0318909 A1 | 12/2009 | Debenedictis et al. |
| 2010/0011236 A1 | 1/2010 | Barthe et al. |
| 2010/0022922 A1 | 1/2010 | Barthe et al. |
| 2010/0160782 A1 | 6/2010 | Slayton et al. |
| 2010/0241035 A1 | 9/2010 | Barthe et al. |
| 2010/0280420 A1 | 11/2010 | Barthe et al. |
| 2011/0112405 A1 | 5/2011 | Barthe et al. |
| 2011/0178444 A1 | 7/2011 | Slayton et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 2000166940 | 6/2000 |
| JP | 2001170068 | 6/2001 |
| JP | 2002028764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2009518126 | 5/2009 |
| JP | 2010517695 | 5/2010 |
| KR | 1020010024871 | 3/2001 |
| KR | 100400870 B1 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9625888 | 8/1996 |
| WO | 9735518 | 10/1997 |
| WO | 9832379 | 7/1998 |
| WO | 9933520 | 7/1999 |
| WO | 9949788 | 10/1999 |
| WO | 0006302 | 2/2000 |
| WO | 0015300 | 3/2000 |
| WO | 0021612 | 4/2000 |
| WO | 0053113 | 9/2000 |
| WO | 0128623 | 4/2001 |
| WO | 0182777 | 11/2001 |
| WO | 0182778 | 11/2001 |
| WO | 0187161 | 11/2001 |
| WO | 0209813 | 2/2002 |
| WO | 0224050 | 3/2002 |
| WO | 02092168 A | 11/2002 |
| WO | 02292168 | 11/2002 |
| WO | 03065347 | 8/2003 |
| WO | 03070105 | 8/2003 |
| WO | 03077833 | 8/2003 |
| WO | 03086215 | 10/2003 |
| WO | 03096883 | 11/2003 |
| WO | 03099177 | 12/2003 |
| WO | 03101530 | 12/2003 |
| WO | 2004080147 | 9/2004 |
| WO | 2004110558 | 12/2004 |
| WO | 2005065408 | 7/2005 |
| WO | 2005090978 | 9/2005 |
| WO | 2006036870 | 4/2006 |
| WO | 2006042168 | 4/2006 |
| WO | 2006042201 | 4/2006 |

(56) References Cited

FOREIGN PATENT DOCUMENTS

| WO | 2006065671 | 6/2006 |
|----|------------|--------|
| WO | 2006082573 | 8/2006 |
| WO | 2009013729 | 1/2009 |

OTHER PUBLICATIONS

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

PCT/US2012/046122 International Search Report Jan. 30, 2013.
PCT/US2012/046123 International Search Report Jan. 28, 2013.
PCT/US2012/046125 International Search Report Jan. 28, 2013.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoacoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Mitragotri, Samir; "Healing sound: the use of ultrasound in drug delivery and other therapeutic applications," Nature Reviews; Drug Delivery, pp. 255-260, vol. 4.

Sanghvi, N.T., et al., "Transrectal Ablation of Prostate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Smith, Nadine Barrie, et al., "Non-Invasive in Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Sassen, Sander, "ATI's R520 architecture, the new king of the hill?" http://www.hardwareanalysis.com/content/article/1813, Sep. 16, 2005, 2 pages.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

Arthur et al., "Non-invasive estimation of hyperthermia temperatures with ultrasound," Int. J. Hyperthermia, Sep. 2005, 21(6), pp. 589-600.

* cited by examiner

ANNULAR ARRAY
(PLAIN VIEW)
PLANAR, FOCUSED
OR DEFOCUSED

SYSTEM AND METHOD FOR VARIABLE DEPTH ULTRASOUND TREATMENT

CROSS-REFERENCE TO RELATED APPLICATIONS

This application is a continuation of U.S. application Ser. No. 10/944,500 entitled "SYSTEM AND METHOD FOR VARIABLE DEPTH ULTRASOUND TREATMENT" filed on Sep. 16, 2004, which application is incorporated herein by reference.

FIELD OF INVENTION

This invention generally relates to an ultrasound system, and more particularly, to a method and system for variable depth ultrasound treatment.

BACKGROUND OF THE INVENTION

Many conventional applications of therapeutic ultrasound have employed low frequency transducers. These transducers have operational frequencies that typically range from 500 kHz to 1.5 MHz. Such low frequency transducers are often preferred because they allow for acoustical energy to be focused deep into the body, without harming the overlying tissue structures.

A conventional application of non-invasive therapeutic ultrasound using a low frequency transducer is depicted in FIG. 1. A conventional therapeutic system 100 comprises a transducer 102 that uses low frequency energy to treat a deep treatment region 110. Deep treatment region 110 is located at a deep depth 106 below a superficial region 112, e.g., tissue layers and structures, and a subcutaneous region 114 of a patient. Deep depth 106 may range from several millimeters to 5-7 centimeters or more. Conventional system 100 cannot treat superficial regions 112 or subcutaneous regions 114 through use of low-frequency transducer 102, thus limiting the applications of such systems. For example, some cosmetic surgeries may also need to provide treatment to superficial and/or subcutaneous, as well as deep treatment regions, thus eliminating the use of lower frequency transducers.

Another undesirable side effect of low-frequency therapy is that the acoustic energy must pass through intervening tissue layers before reaching the desired deep treatment area. The intervening layers tend to defocus the rays and absorb some of the acoustic energy. This causes the focal spot size to widen, making it difficult to control the location of the focal spot.

SUMMARY OF THE INVENTION

In accordance with various aspects of the present invention, a variable depth ultrasound treatment method and system are provided. An exemplary method and system comprise a variable depth transducer system configured for providing ultrasound treatment to more than one region of interest, such as between at least two of a deep treatment region of interest, a superficial region of interest, and/or a subcutaneous region of interest.

In accordance with various exemplary embodiments, a variable depth transducer system can be configured for spatial control, such as by changing the distance from an exemplary transducer to a reflecting surface, or changing the angles of energy focused or unfocused to the region of interest, and/or configured for temporal control, such as by controlling changes in the frequency, drive amplitude and timing of the exemplary transducer. As a result, changes in the location of the treatment region, the shape and size and/or volume of the spot or region of interest, as well as the thermal conditions, can be dynamically controlled versus time.

In accordance with an exemplary embodiment of the present invention, the variable depth transducer can comprise a transduction element having a piezoelectrically active layer, matching layers and/or other materials for generating radiation or acoustical energy. The variable depth transducer may be configured to operate at moderate frequencies to provide variable depth treatment. For example, an exemplary variable depth transducer system can be configured for providing treatment to a superficial region of interest, and/or to a subcutaneous region of interest utilizing moderate frequencies below 20 MHz, such as within a range from approximately 750 kHz to 20 MHz, or higher frequencies of 35 MHz or more.

In accordance with another exemplary embodiment of the present invention, the transduction element may be configured with a variable depth element comprising one or more materials configured to allow for control and focusing/defocusing of the acoustic energy to more than one region of interest, such as between a deep treatment region of interest and a superficial region of interest, and/or a subcutaneous region of interest. The materials utilized for the variable depth element for control and focusing/defocusing may be configured in a variety of manners and shapes, such as substantially flat, curved, or other arrangements for bending, reflecting and/or redirecting radiation and acoustical energy. In addition, the variable depth element may be configured within, or comprise a device coupled to, the transduction element in a variety of manners to provide for focusing/defocusing and control of the treatment energy.

In accordance with another exemplary embodiment of the present invention, an exemplary transducer may be configured to enable energy deposition not only proximate a fundamental frequency of a piezoelectric material within the transduction element, but also at harmonic frequencies of the material, above a fundamental frequency, as well as resonances below a fundamental frequency. These multiple resonances may be controlled and enabled through various focusing techniques and transducer structures, including the adding of matching layers and/or backing layers to shape the resonant characteristics of the transducer.

In accordance with another exemplary embodiment of the present invention, a variable depth acoustic transducer can also be configured for generating high acoustic power for treatment purposes, while also providing for good imaging capabilities. For example, to allow for the treatment spot size to be optimally controlled at various treatment depths, an exemplary embodiment of the present invention may comprise a transducer configured into an array of sub-elements, each sub-element configured for processing acoustic waves with a sufficient bandwidth for good axial resolution.

In accordance with another exemplary embodiment of the present invention, a variable depth transducer may be configured in a probe arrangement to provide treatment. The variable depth transducer may also be configured with various mechanical devices to allow for optimal treatment and therapy, for example to provide controlled positioning of the variable depth transducer, such as through a non-invasive configuration. Further, the variable depth transducer may also be configured for one-dimensional, two-dimensional and annular arrays, and/or for three-dimensional treatment applications.

In accordance with another aspect of the present invention, an exemplary variable depth treatment system and method may also be configured to provide therapeutic heating, cooling and/or imaging of a treatment region as well as acoustically monitoring the temperature profile or other tissue parameter monitoring of the treatment region and the general vicinity thereof. For example, in accordance with an exemplary embodiment, an exemplary variable depth system may be configured with a dynamic feedback arrangement based on monitoring of temperature or other tissue parameters, and/or based on imaging information to suitably adjust the spatial and/or temporal characteristics of the variable depth transducer.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical or treatment contexts, and the exemplary embodiments relating to a variable depth ultrasound treatment as described herein are merely a few of the exemplary applications for the invention. For example, the principles, features and methods discussed may be applied to any medical or other tissue or treatment application.

Figure 1:
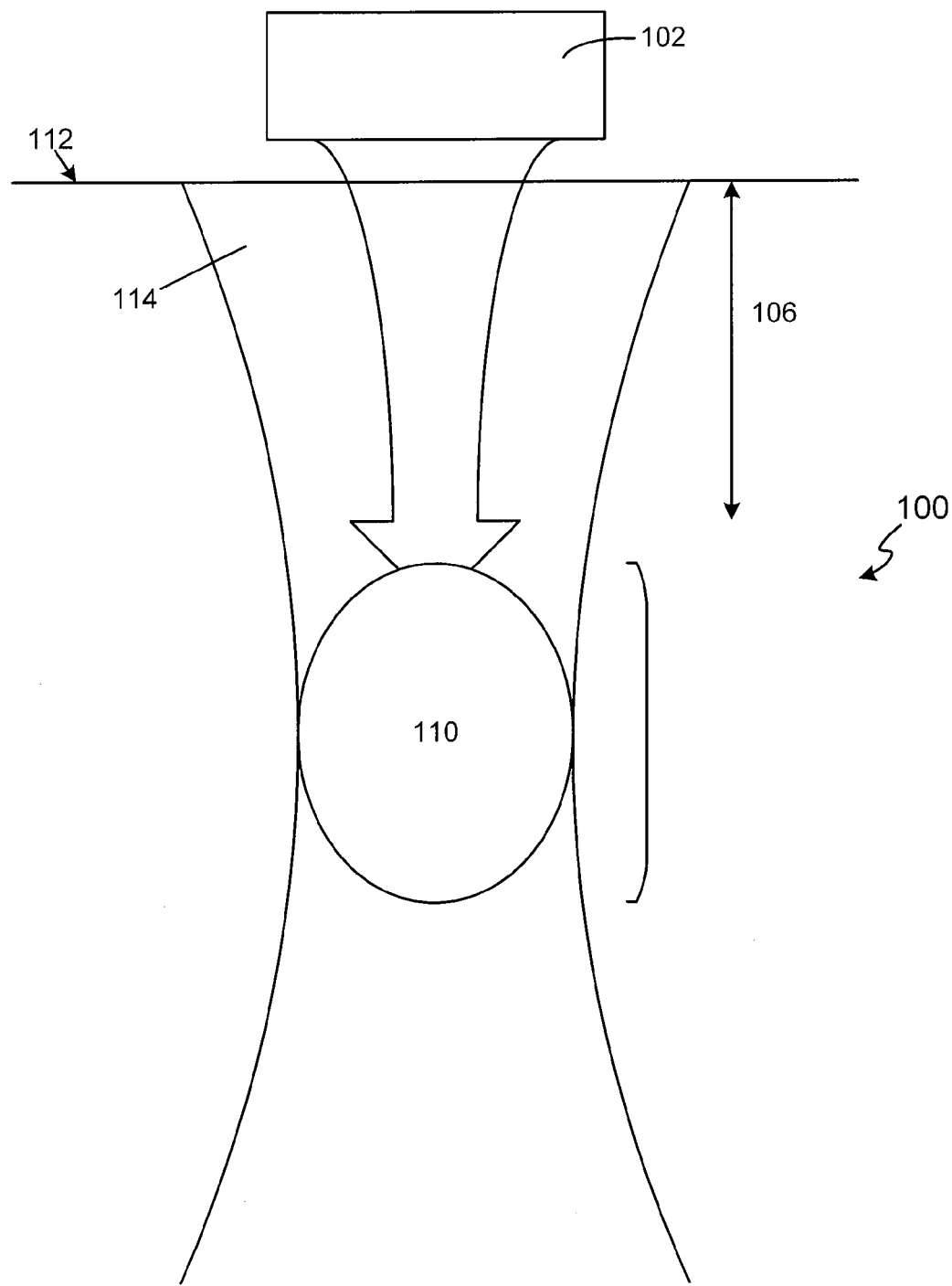
FIG. 1 illustrates a diagram of treatment using a prior art ultrasound treatment system.
Figure 2:
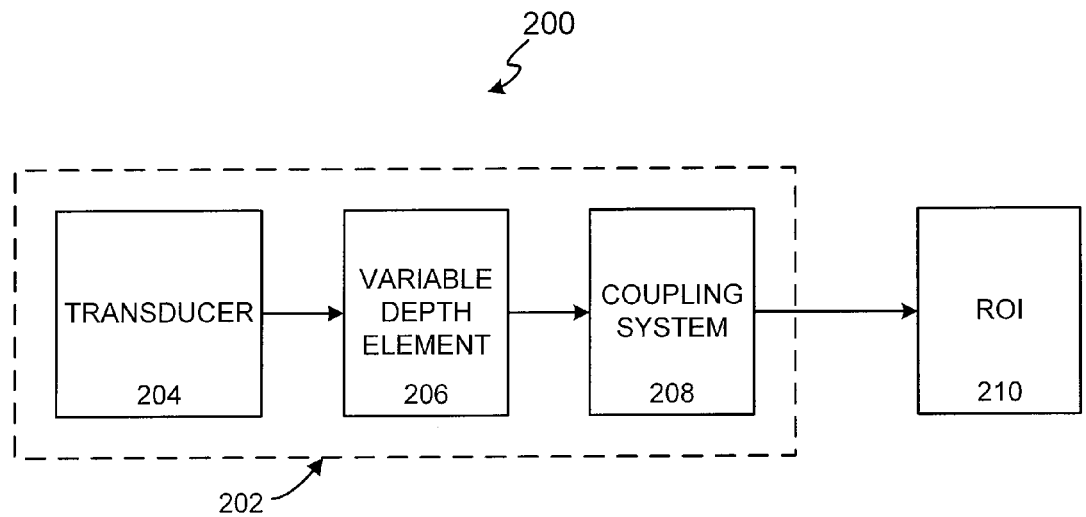
FIG. 2 illustrates a block diagram of an ultrasound treatment system in accordance with an exemplary embodiment of the present invention.

In accordance with various aspects of the present invention, a non-invasive variable depth ultrasound treatment method and system are provided. An exemplary method and system comprise a variable depth acoustic transducer system configured for providing ultrasound treatment to more than one region of interest in a patient. For example, with reference to an exemplary embodiment illustrated in a block diagram of FIG. 2, an exemplary system 200 for ultrasound treatment includes a variable depth transducer system 202 that provides treatment to a region of interest 210. Variable depth transducer system 202 may comprise a transducer 204 configured with a variable depth device 206. In providing treatment, variable depth ultrasound system 202 may provide therapy, imaging and/or temperature or other tissue parameter monitoring to region of interest 210. Region of interest 210 can comprise a deep treatment region, a superficial region, and/or a subcutaneous region of interest or any other region of interest located within a patient. To facilitate coupling of variable depth ultrasound system 202 to region of interest 210, variable depth ultrasound system 202 can further comprise a coupling system 208 configured for acoustic coupling of ultrasound energy and signals.

Figure 3:
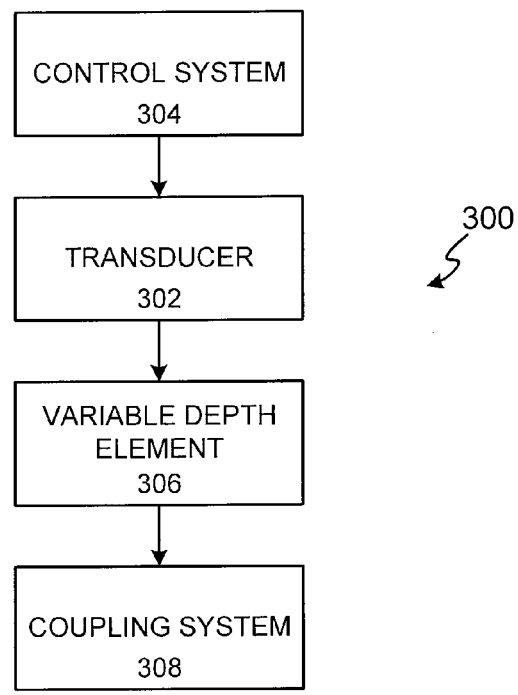
FIG. 3 illustrates a block diagram of a variable depth ultrasound treatment system in accordance with an exemplary embodiment of the present invention.

An exemplary variable depth transducer system 300 is further exemplified in a block diagram illustrated in FIG. 3. Variable depth transducer system 300 may comprise a control system 304, a transducer 302, a variable depth element 306, and a coupling system 308. Control system 304 is configured for control and operation of transducer 302 to provide treatment to more than one region of interest. Transducer 302 and variable depth device 306 are configured to provide variable depth ultrasound treatment to a treatment region. Coupling system 308 is configured for coupling of transducer 302 and variable depth device 306 to a region of interest.

Control system 304 may be configured for use within an ultrasound therapy system, an ultrasound imaging system, and/or an ultrasound imaging, therapy and/or treatment monitoring system, including motion control subsystems. In accordance with an exemplary embodiment, a control system 304 may comprise a processor, a display, and/or one or more input devices. The processor may comprise a personal computer, a Unix system, or any other conventional processing unit. The display may comprise a monitor, LCD screen, or any other device configured to display an image. An input/output device may comprise a keyboard, a mouse, a touchscreen, or any other device for inputting information. The information from the input device and images displayed may be received or transmitted in any format, such as manually, by analog device, by digital device, and/or by any other mechanisms. The processor, display, and/or input device may be coupled together in any manner. By coupling, the devices comprising control system 304 may be directly connected to each other or may be connected through one or more other devices or components that allow a signal to travel to/from one component to another. The various coupling components for the devices comprising control system 304 can include but are not limited to the internet, a wireless network, a conventional wire cable, an optical cable or connection through any other medium that conducts signals, and any other coupling device or communication medium.

Coupling system 308 is configured for the coupling ultrasound energy and signals between transducer 302 and variable depth device 306 and a region of interest. Coupling system 308 may facilitate such coupling through use of various coupling mediums, including air and other gases, water and other fluids, gels, solids, and/or any combination thereof, or any other medium that allows for signals to be transmitted between transducer 302/variable depth device 306 and the region of interest. In addition to providing a coupling function, in accordance with an exemplary embodiment, coupling system 308 can also be configured for providing temperature control during the treatment application. For example, coupling system 308 can be configured for controlled cooling of an interface surface or region between transducer 302/variable depth device 306 and the region of interest by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial control of variable depth transducer system 300.

Exemplary variable depth transducer 302 can be configured in various manners. For example, a variable depth transducer system can be configured for spatial control, such as by controlled changing of the distance from an exemplary transducer to a reflecting surface, or controlled changing of the angles of energy focused or unfocused to the region of interest, e.g., variable depth transducer 302 can be configured with variable depth element 306 comprising a frequency dependent lens configured for control of focal depth and position by changing the frequency of excitation of variable depth transducer 302. In addition, variable depth transducer 302 can also be configured for temporal control, such as by controlling changes in the frequency, drive amplitude and timing of the exemplary transducer. Thus, an exemplary variable depth transducer can be configured with spatial and/or temporal control. As a result, changes in the location of the treatment region, the shape and size and/or volume of the spot or region of interest, as well as the thermal conditions, can be dynamically controlled versus time.

Variable depth element 306 can be suitably coupled to transducer 302 to facilitate variable depth treatment. By coupling, transducer 302 may be directly and/or movably connected to variable depth device 306, or may be connected through one or more various components or elements that enable energy and/or signals to travel to/from one component to another. Transducer 302 and variable depth element 306 may also be combined into a single device, wherein variable depth device 306 is configured within transducer 302, e.g., as a part of a transduction element of transducer 302.

Figure 4:
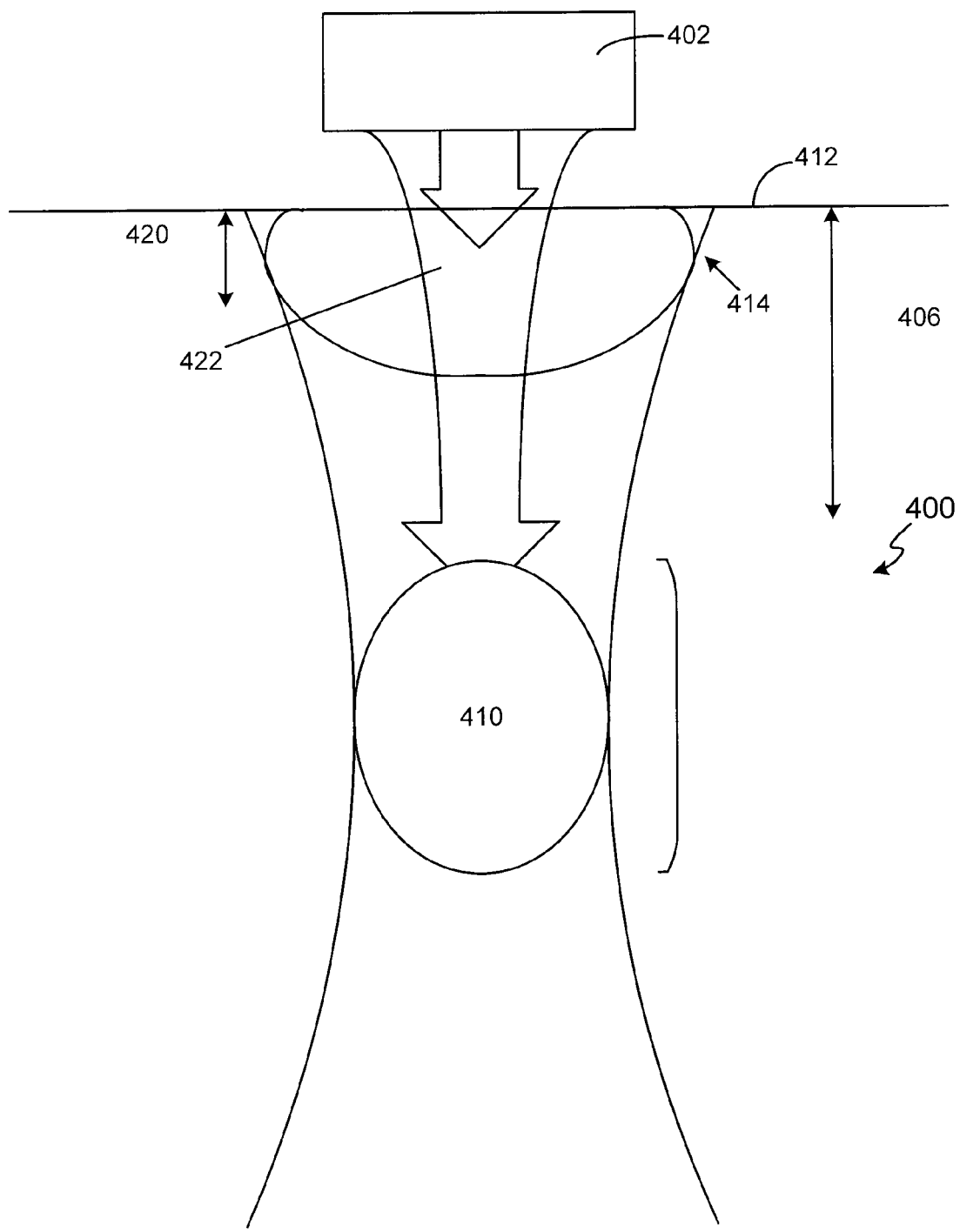
FIG. 4 illustrates a diagram of a variable depth ultrasound treatment system in accordance with an exemplary embodiment of the present invention.

Variable depth element 306 is configured to enable variable depth treatment system 300 to provide treatment to more than one region of interest, such as between a deep treatment region of interest, a superficial region of interest, and/or a subcutaneous region of interest, or other regions in between. Such treatment can occur within a single region of interest, or within more than one region of interest, at the same time. For example, with momentary reference to FIG. 4, an exemplary embodiment of a variable depth treatment system 400 is shown. Variable depth treatment system 400 may be configured for operating within moderate frequencies ranging from approximately 750 kHz to 20 MHz or more. Variable depth treatment system 400 may be configured with a variable depth transducer system 402 comprising a transducer configured with a variable depth device. Variable depth transducer system 402 may be coupled to a control system for receiving and transmitting signals to/from a region of interest.

During operation, variable depth transducer system 402 may be configured to transmit or receive signals to treat a deep treatment region 410 located at deep depth 406 within a patient. For example, depth 406 for deep treatment region 410 may range from approximately 50 mm to 7 cm or more.

Variable depth transducer system 402 may also be configured to treat a second inner region 422 of a patient. Inner region 422 may comprise a superficial layer 412 of a patient and/or a subcutaneous layer 414 of patient. Inner region 422 is located at a shorter depth 420 within tissue layers of a patient. For example, depth 420 may range from approximately 0 mm to 5 cm or more within a patient, wherein the 0 mm range comprises the outer surface of superficial layer 412 of the patient. In other words, superficial layer 412 of the patient may comprise any area on or near the surface of the patient. Treatment by variable depth treatment system 400 may include treatment of both deep region 410 and inner region 422, or within only one region of interest.

Variable depth element 306 can be configured in various manners to facilitate treatment of more than one region of interest, such as inner region 422 and/or deep-seated region 410. In accordance with an exemplary embodiment of the present invention, transducer 302 may be configured with variable depth element 306 comprising one or more materials configured to allow for control and focusing/defocusing of the acoustic energy to more than one region of interest. For example, with reference to exemplary embodiments illustrated in FIGS. 5A and 5B, a variable depth transducer system 500 can comprise a transducer 502, electrical leads 510, and a variable depth device 528 or 530 suitably configured with transducer 502 to facilitate treatment.

Transducer 502 can include a transduction element comprising a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to or instead of a piezoelectrically active material, variable depth transducer 502 may comprise any other materials configured for generating radiation and/or acoustical energy. Variable depth transducer 502 may also comprise one or more matching layers and/or backing layers to suitably shape the resonant character of transducer 502. For example, variable depth transducer 502 may be configured, along with transduction element, with one or more matching layers and/or backing layers coupled to a piezoelectrically active material or any other material configured for generating radiation and/or acoustical energy.

For temporal control, the thickness of the transduction element of variable depth transducer 502 may be selected to provide a center operating frequency of moderate range, for example from approximately 750 kHz to 30 MHz or more. Lower frequencies, e.g., between approximately 750 kHz and 8 MHz, can facilitate deeper penetration and higher frequencies, e.g., between approximately 8 to 20 MHz or more, can facilitate greater resolution. Selecting the frequency for operation can be based on the degree and balance of energy penetration and resolution that is desired for an application.

Electrical leads 510 may be configured to enable power to be transmitted to and signals received from variable depth transducer 502, and can comprise any wiring type, configuration and arrangement for use with ultrasound transducers. Variable depth transducer 502 may also be coupled to electrical leads 510 in various manners. For example, while FIG. 5 depicts electrical leads 510 coupled to only one end of variable depth transducer 502, electrical leads 510 may also be coupled together on an opposite end, or any other location along variable depth transducer 502.

To facilitate spatial control, in an exemplary embodiment, variable depth device 528 can comprise one or more reflective materials 504 configured to provide control and focusing of acoustic or radiation energy from variable depth transducer 502 towards a region of interest 518. In accordance with an exemplary embodiment, reflective materials 504 can comprise acoustic mirrors, lenses, reflectors or prisms configured for focusing of acoustic or radiation energy. The exemplary mirrors, reflectors or prisms may comprise any material for reflecting, bending or redirecting acoustic or radiated energy. For example, such materials may include stainless steel, aluminum, or any other metal alloy, glass, plastic, or any other material capable of bending, redirecting and/or reflecting back acoustical energy from a surface to another direction.

In accordance with one exemplary embodiment, reflective materials 504 may be suitably inclined at approximately a 45 degree angle with respect to variable depth transducer 502; however, reflective materials 504 may be configured to be inclined at any angle with respect to variable depth transducer 502 such that energy transmitted from variable depth transducer 502 is bent, redirected or reflected from reflective materials 504 towards a region of interest 518. Changing the angle of inclination can suitably control the focusing of acoustic energy to any one region of interest 518, such as to a deep treatment region of interest, a superficial region of interest, or a subcutaneous region of interest.

Figure 5B:
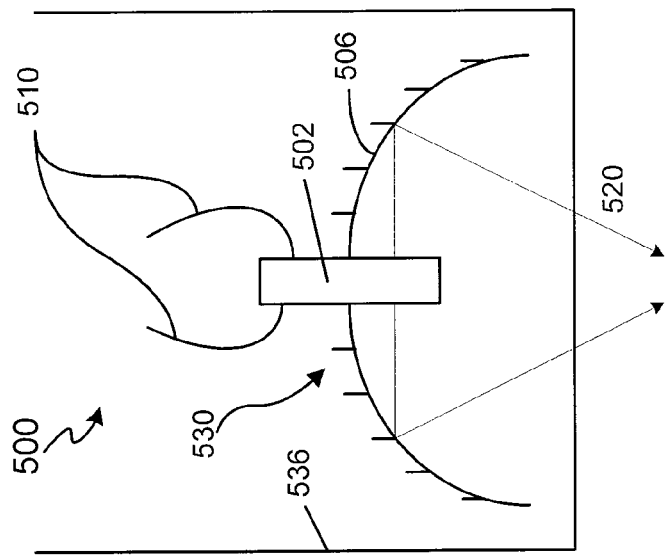
FIGS. 5A and 5B illustrate exemplary embodiments for variable depth ultrasound transducers for treatment in accordance with the present invention.

Variable depth devices 528 and 530 may be configured in a variety of manners, such as substantially flat, curved, or other suitable arrangements for reflecting, bending or redirecting acoustic or radiated energy. For example, with reference to FIG. 5A, variable depth device 528 can comprise mirrors 504 configured in a substantially flat manner. However, with reference to FIG. 5B, variable depth device 530 can also comprise mirrors 506 configured in a curved arrangement to allow for focusing of energy from variable depth transducer 502 to a region of interest 520. While FIG. 5B illustrates mirrors 506 as substantially spherical and symmetric, mirrors 506 may also be curved in an aspherical and/or asymmetric manner such that energy transmitted from variable depth transducer 502 is bent, redirected, or reflected from mirrors 506 towards a region of interest 520. Still further, mirrors 506 can also be configured in other shapes and arrangements, such as jagged, saw tooth, wavy or other non-planar surfaces, or any other surface or compound surfaces configured for reflecting, bending or redirecting acoustic or radiated energy.

Figure 5A:
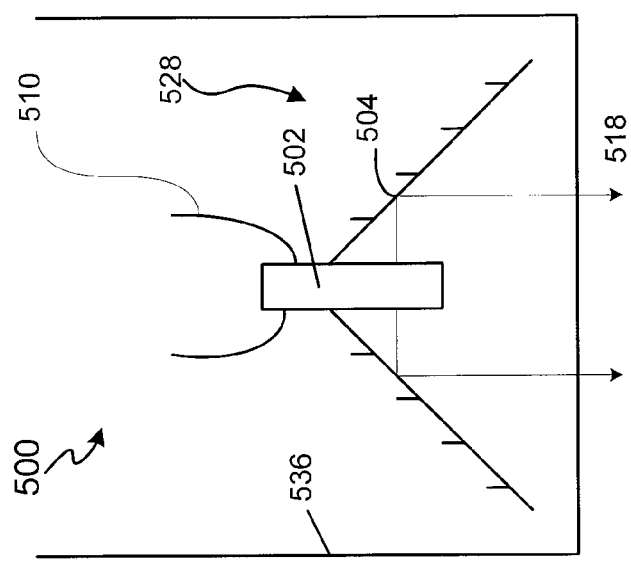

Moreover, while FIG. 5A depicts variable depth device 528 with mirrors 504 configured to be substantially flat, and FIG. 5B depicts variable depth device 530 with mirrors 506 configured to be curved, variable depth devices 528, 530 may also be configured with any combination of substantially flat, curved mirrors, and/or other planar, non-planar or other arrangements for facilitating spatial control. In accordance with an exemplary embodiment utilizing spatial and temporal control, variable depth devices 528 and 530 can be configured with a frequency dependent mirror or lens configured for spatial control of the focal depth and position by changing the frequency of excitation of variable depth transducer 502.

As a result, an exemplary transducer system 500 can be configured for providing treatment to a superficial region of interest and/or to a subcutaneous region of interest utilizing moderate frequencies below approximately 20 MHz. For example, an exemplary transducer system 500 can provide treatment to superficial regions and/or to subcutaneous regions that are more commonly addressed in cosmetic applications with an operating frequency range from approximately 750 kHz to 35 MHz or more.

Variable depth transducer system 500 can be configured in various arrangements to provide non-invasive treatment. For example, in accordance with an exemplary embodiment, variable depth devices 528, 530 may be configured with variable depth transducer 502 within a housing 536. Housing 536 can comprise any configuration of transducer housing for containing transducers and for interfacing with a patient to allow treatment, such as facilitate non-invasive treatment. Coupling of signals from transducer 502 and variable depth devices 528, 530 through housing 536 to a region of interest may be facilitated through any coupling medium, such as air and other gases, water and other fluids, gels, solids, any combination thereof, and/or any other medium that allows for signals to be transmitted from transducer 502/variable depth devices 528, 530 to a region of interest.

In addition to comprising separate devices and components, variable depth transducer 302 and variable depth element 306 may also comprise the same device, i.e., variable depth element 306 is configured within transducer 302. For example, with reference to an exemplary embodiment illustrated in FIG. 6, a variable depth transducer system 600 can comprise a variable depth transducer 602 configured as a variable depth device to provide for control and focusing of acoustic energy 620 towards a region of interest 630.

Variable depth transducer 602 may comprise a transduction element comprised of a piezoelectrically active material, such as lead zirconante titanate (PZT), or any other piezoelectrically active material, such as a piezoelectric ceramic, crystal, plastic, and/or composite materials, as well as lithium niobate, lead titanate, barium titante, and/or lead metaniobate. Variable depth transducer 602 may also comprise one or more matching and/or backing layers configured along with the piezoelectrically active material. In addition to or instead of a piezoelectrically active material, variable depth transducer 602 may comprise any other materials configured for generating radiation and/or acoustical energy.

In accordance with an exemplary embodiment, variable depth transducer 602 is configured in a curved manner to enable focusing of acoustic energy 620 to region of interest 630. The curvature can be substantially spherical and/or symmetric manner, or curved in an aspherical and/or asymmetric manner. Furthermore, variable depth transducer 602 can comprise any other configuration to enable focusing of acoustic energy 620 to region of interest 630, such as to a deep treatment region of interest, a superficial region of interest, and/or a subcutaneous region of interest. For example, variable depth transducer 602 can be configured in any planar or non-planar arrangement.

For temporal control, the thickness of the transduction element of variable depth transducer 602 may be selected to provide a center operating frequency of moderate range, for example from approximately 750 kHz to 20 MHz. Lower frequencies, e.g., between approximately 750 kHz and 8 MHz, can facilitate deeper penetration and higher frequencies, e.g., between approximately 8 to 30 MHz or more, facilitate greater resolution. As a result, an exemplary transducer system 600 can be configured for providing treatment to a superficial region of interest and/or to a subcutaneous region of interest utilizing moderate frequencies below 20 MHz. For example, an exemplary transducer system 600 can provide treatment to superficial regions and/or to subcutaneous regions that are more commonly addressed in cosmetic applications with an operating frequency range from approximately 750 kHz to 1.5 MHz or more.

Figure 6:
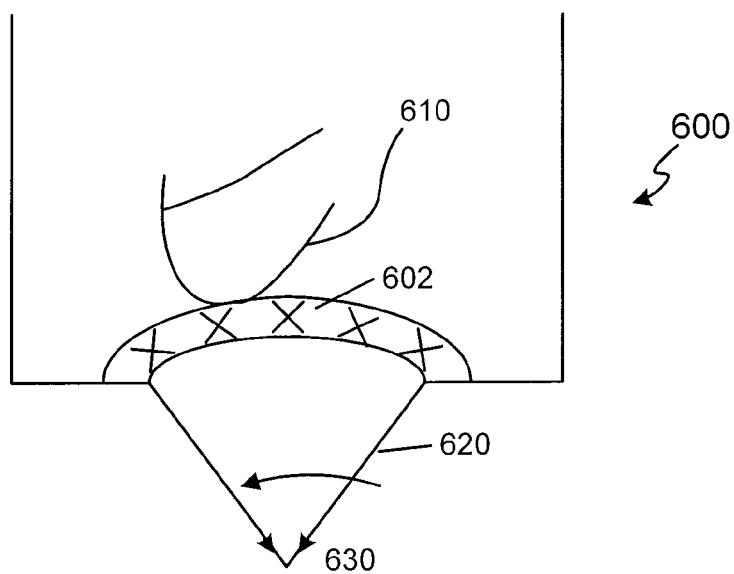
FIG. 6 illustrates another exemplary embodiment for a variable depth ultrasound transducer for treatment in accordance with the present invention.

Electrical leads 610 are configured to enable power to be transmitted to and signals received from variable depth transducer 602, and can comprise any wiring type, configuration and arrangement for use with ultrasound transducers. Variable depth transducer 602 may also be coupled to electrical leads 610 in various manners. For example, while FIG. 6 depicts electrical leads 610 coupled to only one side of variable depth transducer 602, electrical leads 610 may also be coupled together on an opposite end, or any other location along variable depth transducer 602.

Figure 7:
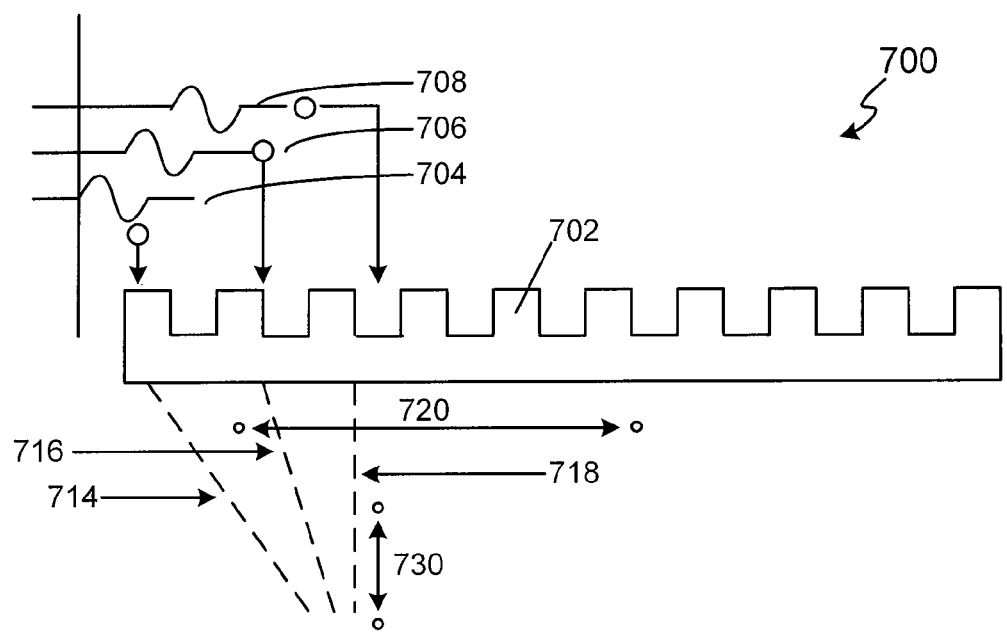
FIG. 7 illustrates an exemplary embodiment for electronic focusing of a transducer in accordance with the present invention.

In addition to having a variable depth transducer 602 configured as a variable depth device to provide for control and focusing of acoustic energy 620 towards a region of interest 630, in accordance with an exemplary embodiment, a variable depth transducer may also be configured electronically to provide for control and focusing of acoustic energy. For example, with reference to an exemplary embodiment depicted in FIG. 7, an exemplary electronic focusing transducer system 700 is illustrated. Electronic focusing transducer system 700 is configured with a variable depth transducer 702. Like transducers 502 and 602, variable depth transducer 702 may comprise a piezoelectrically active material, composite materials, one or more matching layers, and/or any other materials configured for generating radiation and/or acoustical energy. Variable depth transducer 702 may also comprise a one-dimensional or two-dimensional array of transducers.

In accordance with an exemplary embodiment, variable depth transducer 702 comprises one or more transducers and/or transduction elements that can be activated by various drive frequencies with suitable phase delay. For example, variable depth transducer 702 can be activated by a first drive frequency 704, and then subsequently activated by at least one or more delayed drive frequencies 706 or 708. The phase delay in drive frequencies allows for focusing of acoustical energy to occur both tangentially 720 and axially 730.

The drive frequencies 704, 706, 708 transmitted to variable depth transducer 702 may comprise substantially similar frequencies and/or different frequencies, wherein all frequencies are in the moderate range, i.e., between approximately 750 kHz to 20 MHz. The delay between drive frequencies 704, 706, 708 may range from 0 ms to approximately a full period of the drive frequency. For example, the delay may comprise zero or approximately $1/1000$th of a drive frequency period up to $15/16^{th}$, $31/32^{nd}$ or more of a drive frequency period, with variations comprising any fraction of a full wavelength in time delay.

Electronic phase delay focusing of variable depth transducer 702 may be done tangentially and/or axially. For example, drive frequencies 704, 706, 708 and/or the phase associated with drive frequencies 704, 706, 708 may be varied to provide focusing tangentially and/or axially. In accordance with an exemplary embodiment, variable depth transducer 702 may comprise subapertures that may be turned on and off to also provide focusing tangentially and/or axially. Phased focusing may prevent over-treatment of a region of interest by automating the focus and treatment times for a treatment region. Thus, for example, electronic control of variable depth transducer 702 may be facilitated by shunting various subapertures together to control the effective acoustic size of the source/receiver.

Thus, an exemplary transducer system can comprise a variable depth transducer 502, 602, 702 or any other transducer configuration for providing control and focus of acoustical and radiation energy to more than one region of interest within a patient. Such an exemplary transducer system can comprise a transducer configured with or coupled to a variable depth device or feature to provide energy to more than one region of interest. Moreover, an exemplary transducer system can provide treatment to superficial regions and/or to subcutaneous regions that are more commonly addressed in cosmetic applications with an operating frequency range below 30 MHz, or more, even from approximately 750 kHz to 8 MHz that is not attainable by prior art low-frequency transducers.

In accordance with another aspect of the present invention, a variable depth acoustic transducer can also be configured for generating high acoustic power for treatment purposes, while also providing for good imaging capabilities. To allow for the treatment spot size to be optimally controlled at various treatment depths, an exemplary embodiment of the present invention may comprise a transducer configured into an array of sub-elements.

For example, in accordance with an exemplary embodiment with reference again to FIG. 6, variable depth transducer 602 can comprise a plurality of sub-transduction elements, wherein any of the plurality of sub-transduction elements may be configured to provide for focusing energy 620, e.g., any of the plurality of sub-transduction elements can be configured for processing acoustic waves with a sufficient bandwidth for good axial resolution. The sub-transduction elements may be configured such that all are curved, e.g., with the same or varying curvatures, or with one or more sub-transduction elements being substantially flat, with the remaining sub-transduction elements being curved. Further, the sub-transduction elements can be configured in any other shapes configured to provide for control and focusing of acoustic energy 620 towards a region of interest 630.

In accordance with another exemplary embodiment of the present invention, an exemplary variable depth transducer system 300 may be configured to enable energy deposition not only proximate a fundamental frequency of a piezoelectric material within the transduction element, but also at other frequencies, such as harmonic frequencies of the material, above a fundamental frequency, as well as resonances below a fundamental frequency. These harmonic and below fundamental resonances may be controlled and enabled through various focusing techniques and transducer structures, including the adding of matching layers and/or backing layers to shape the resonant characteristics of the transducer.

For example, energy can be suitably provided to a treatment region at a frequency near the peak acoustic output or peak acoustic transmit efficiency of transducer 302 when a piezoelectrically active material is driven near its fundamental frequency. Different sized and shaped piezoelectric materials have different fundamental frequencies for various electrode configurations. In accordance with an exemplary embodiment, energy can also be deposited when the piezoelectric material is driven above its fundamental frequency, e.g., at harmonics, or when driven below the fundamental frequency. The use of the multiple frequency characteristics of transducer 302 may be controlled and enabled through various transducer configurations, acoustic control and/or focusing techniques.

Figure 8:
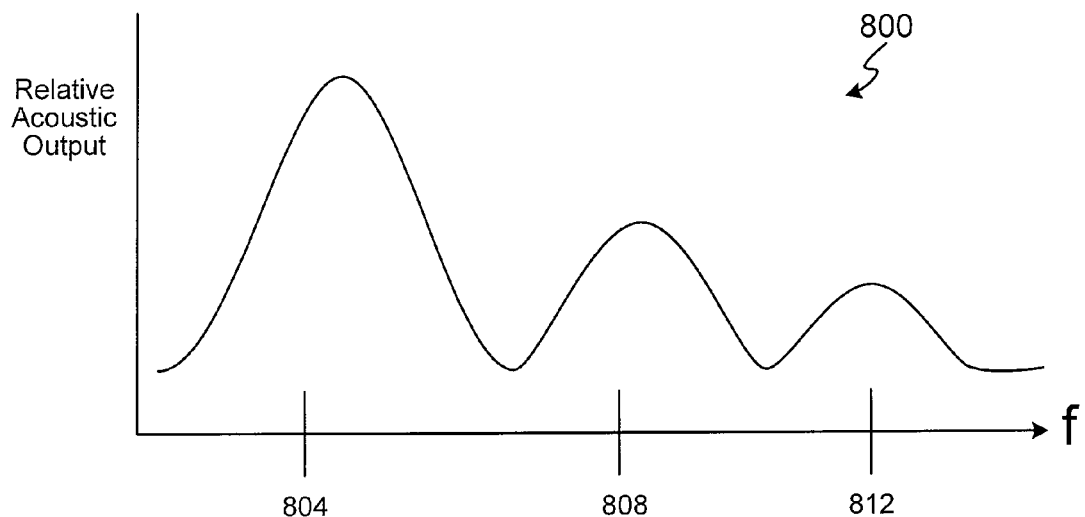
FIG. 8 illustrates an exemplary diagram of treatment characteristics of an exemplary transducer operating at the fundamental frequency and other frequencies and/or resonances above and below the fundamental in accordance with the present invention.

In accordance with an exemplary embodiment, the multiple frequencies may be enabled through the concentration of acoustic energy through the variable depth device 306. Enablement of the multiple frequencies allows for treatment at various depths corresponding to the different frequencies. For example, with additional reference to the acoustic output versus frequency curve illustrated in FIG. 8, variable depth transducer system 300 may treat multiple regions, represented by curve 800. Driving moderate frequencies through transducer 302 and variable depth device 306 may enable treatment of a first deep region 804, treatment of a second shallower region 808, and treatment of a third inner region 812. With respect to treatment techniques, various therapy, imaging and/or temperature monitoring applications may be provided to regions 804, 808, and/or 812. While three treatment regions are depicted in FIG. 8, variable depth transducer system 300 may be configured to enable multiple frequencies for treatment of two, four, or more regions.

In accordance with another aspect of the invention, the variable depth transducer 302 may be configured to provide one, two or three-dimensional treatment applications for focusing acoustic energy to one or more regions of interest. For example, as discussed above, variable depth transducer 302 can be suitably diced to form a one-dimensional array, e.g., transducer 602 comprising a single array of sub-transduction elements.

Figure 9:
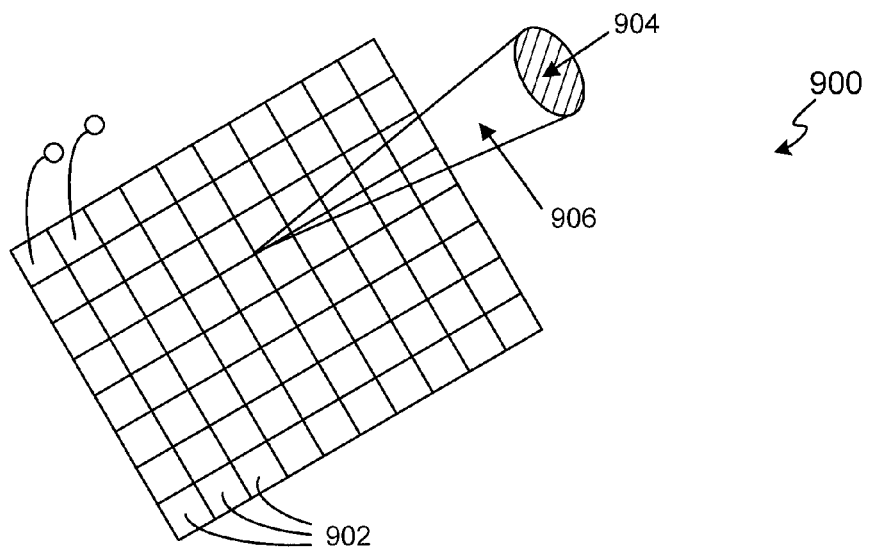
FIG. 9 illustrates an exemplary embodiment of a two-dimensional array in accordance with the present invention.

In accordance with another exemplary embodiment, variable depth transducer 302 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904 of the treatment region. As a result, the two-dimensional array 900 can provide a two-dimensional slicing of the image place of a treatment region, thus providing two-dimensional treatment.

In accordance with another exemplary embodiment, variable depth transducer 302 may be suitably configured to provide three-dimensional treatment. For example, to provide-three dimensional treatment of a region of interest, with reference again to FIG. 3, a three-dimensional system can comprise variable depth transducer 302 configured with an adaptive algorithm, such as, for example, one utilizing three-dimensional graphic software, contained in a control system, such as control system 304. The adaptive algorithm is suitably configured to receive two-dimensional imaging, temperature and/or treatment information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

Alternatively, rather than utilizing an adaptive algorithm, such as three-dimensional software, to provide three-dimensional imaging and/or temperature information, an exemplary three-dimensional system can comprise a single variable depth transducer 302 configured within a probe arrangement to operate from various rotational and/or translational positions relative to a target region.

Figure 10:
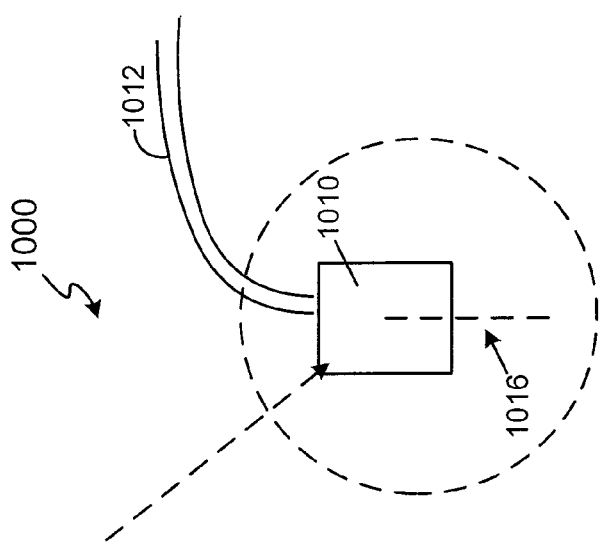
FIG. 10 illustrates an exemplary embodiment of a probe format for treatment in accordance with the present invention.

For example, with reference to FIG. 10, a probe 1010 can be configured to rotate around a perimeter of a treatment region 1014 to provide three-dimensional imaging and temperature information. Probe 1010 may comprise a variable depth transducer system, such as, for example with reference to FIG. 3, variable depth transducer 302 configured with variable depth device 306. In the exemplary embodiment, probe 1010 may be coupled to control system 304 through a connector 1012. Connector 1012 may comprise a wire, optical cable, wireless connection, or any other device capable of sending and/or receiving information from control system 304 to variable depth transducer 302 and variable depth device 306 housed within probe 1010.

Probe 1010 may be configured to rotate around an axis 1016 to provide three-dimensional information. The rotational movement can comprise movement in either a clockwise or counterclockwise direction, or both. Further, the rotational movement could include complete or partial rotations. Thus, the rotational movement could include movement between only two positions, or between any other number of rotational positions. Still further, probe 1010 can be configured to translate or sweep along axis 1016 to provide a larger field-of-view and thus facilitate additional three-dimensional information. Accordingly, the probe system 1000 may comprise rotational and/or translational movement suitably configured to provide three-dimensional information.

Figure 11:
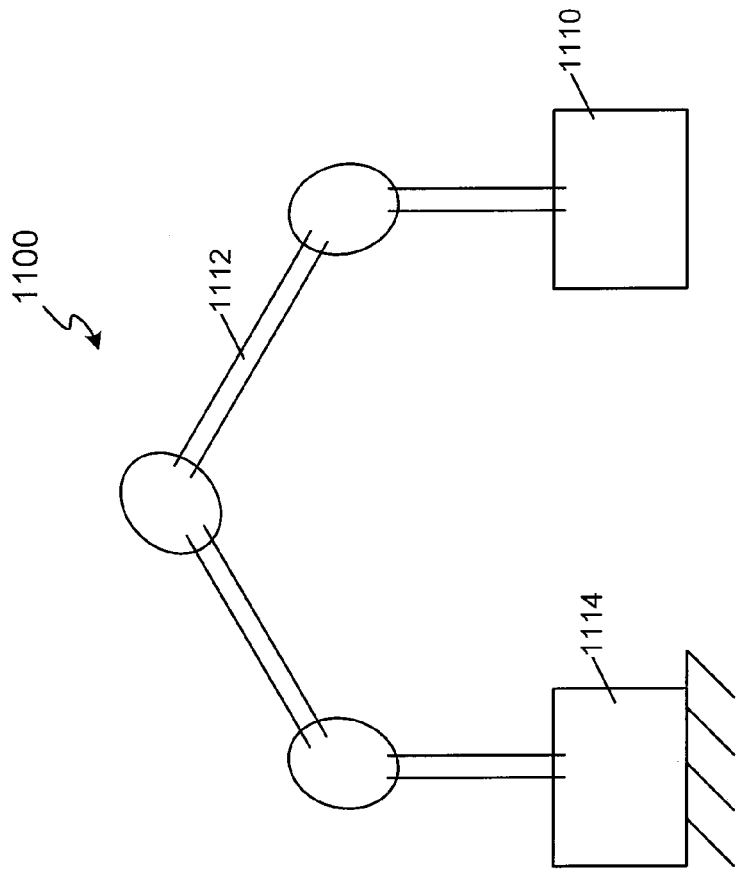
FIG. 11 illustrates an exemplary embodiment of a mechanism for treatment in accordance with the present invention.

Rotational and/or translational movement of probe 1010 may be controlled by manually placing probe 1010 in various desired rotational positions around the treatment region 1014. The movement of variable depth transducer 302 within probe 1010 in various rotational and/or translational positions can also be controlled by any mechanical scanning device now known or hereinafter devised for automated movement. For example, with reference to an exemplary embodiment illustrated in FIG. 11, automated rotational and/or translational movement may be achieved through use of a robotic arm mechanism 1100. Robotic arm mechanism 1100 comprises a manually and/or electromechanically actuated robotic arm 1112 coupled with a probe 1110 and a control 1114.

Probe 1110 may comprise a variable depth transducer system, such as variable depth transducer 302 configured with variable depth device 306. Movement of probe 1110 is mechanically provided through the operation of robotic arm 1112. Robotic arm 1112 may comprise one or more sub-segments that allow precise movement and precise measurement of position in one or more up to any direction. Robotic arm 1112 may be driven by control system 1114. Control system 1114 may comprise a drive box, gears or any other device for providing mechanical movement of robotic arm 1112. Control system 1114 may also comprise a processor, a display, and/or an input/output device. Probe 1110 may be further coupled to control system 1114 through a wire or optical cable configured alongside or within robotic arm 1112, a wireless connection, or any other device capable of sending and/or receiving information from control system 1114 to variable depth transducer 302 and variable depth device 306 housed within probe 1110.

Control system 1114 may provide movement and control of robotic arm 1112 with up to six degrees of freedom. Control system 1114 may allow for movement of robotic arm 1112 to be referenced with one or more fixed positions in space. Control system 1114 may also allow for movement of robotic arm 1112 to be referenced with one or more fixed positions on a patient.

While the three-dimensional systems may include a single acoustic transducer configured with a two-dimensional array 900 and an adaptive algorithm to provide three-dimensional imaging, temperature monitoring and therapeutic heating to a treatment region; the three-dimensional system may also be configured to include both an adaptive algorithm and rotational and/or translational movement to provide additional information. As such, an even larger area of treatment may be obtained through the use of both the adaptive algorithm and the rotational and/or translational movement.

Continuing with this example, the three-dimensional system can be suitably configured to capture imaging and temperature information and provide therapeutic heating from variable depth transducer 302 once variable depth transducer 302 becomes fixedly maintained at various rotational positions. The three-dimensional system can also be suitably configured to capture imaging and temperature information and provide therapeutic heating just prior to, or just after, becoming fixedly positioned. The three-dimensional system can also be configured to capture imaging and temperature information and provide therapy during movement around the various rotational positions.

Figure 12A:
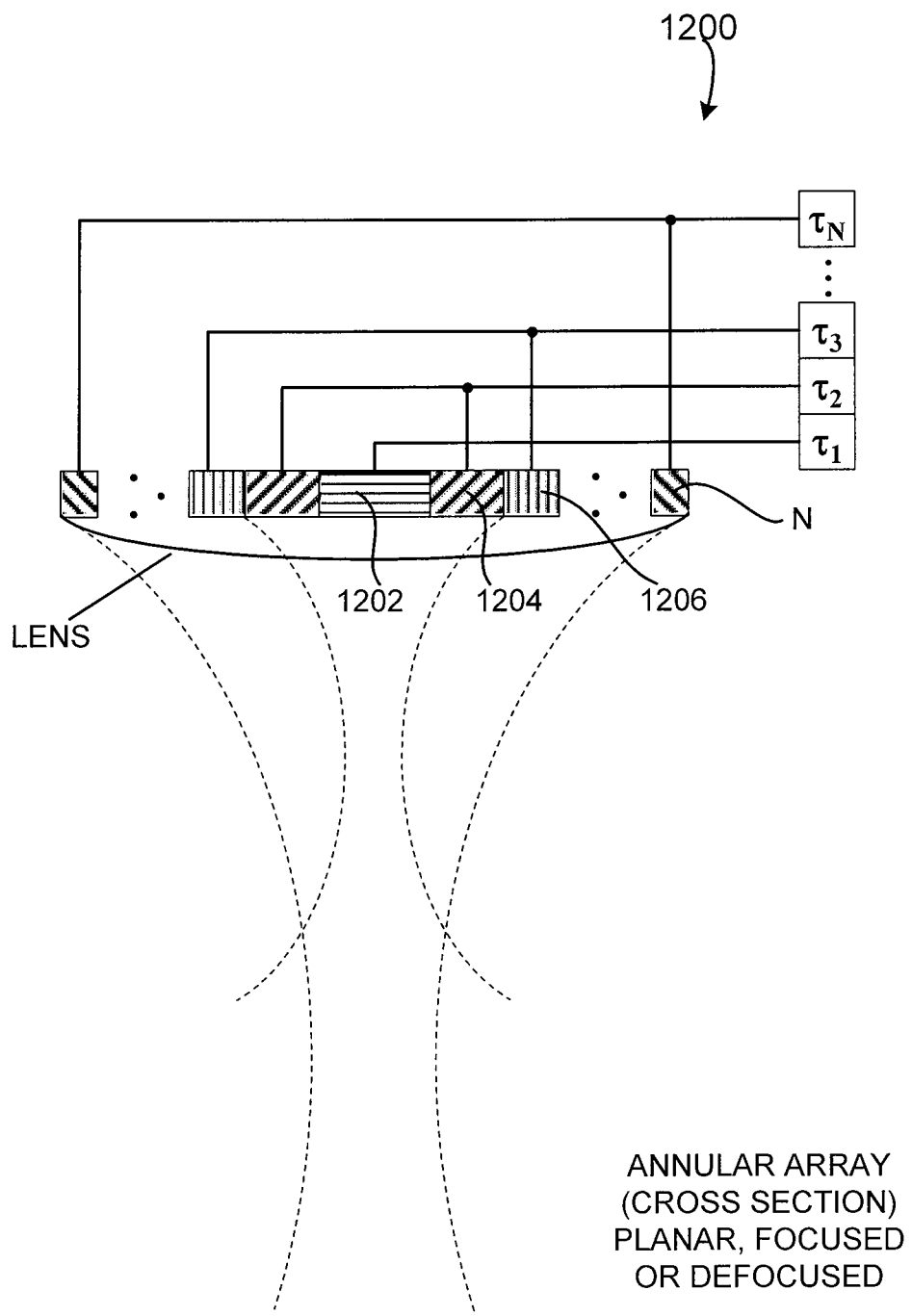
FIGS. 12A and 12B illustrate an exemplary embodiment of an annular array in accordance with the present invention.
Figure 12B:
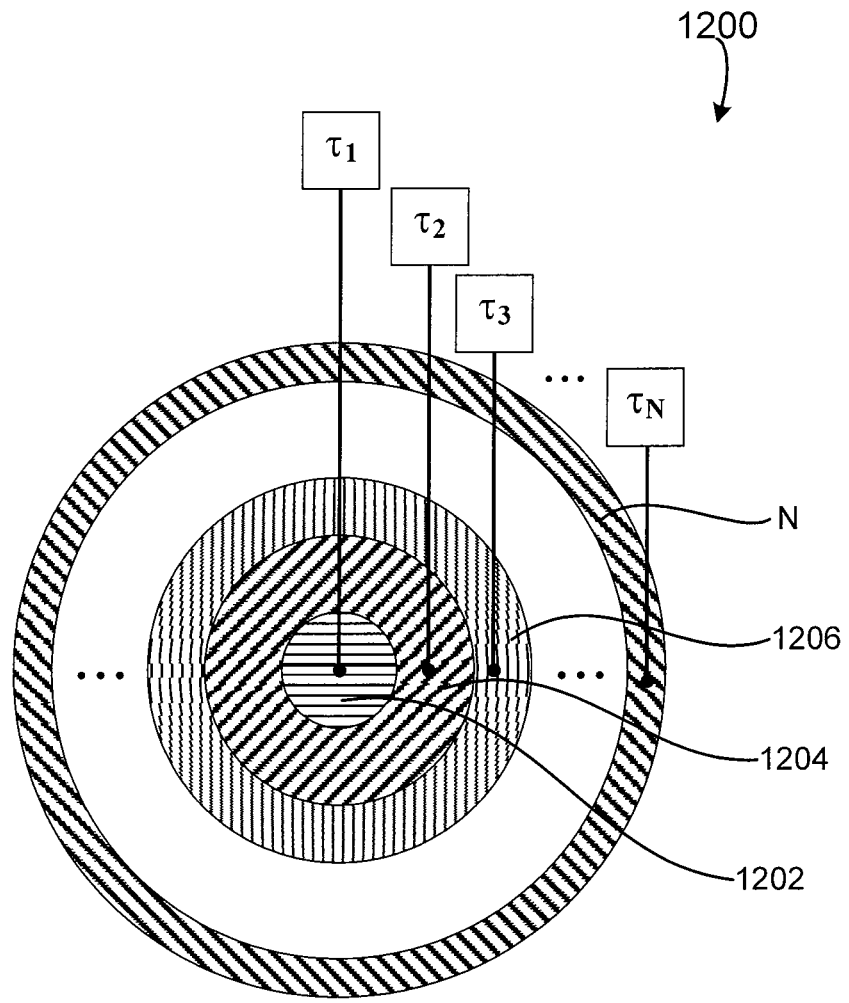

In addition to one, two or three-dimensional arrays, an exemplary variable depth transducer can also be configured within an annular array to provide planar, focused and/or defocused acoustical energy to more than one region of interest. For example, in accordance with an exemplary embodiment, with reference to FIGS. 12A and 12B, an annular array 1200 comprising a plurality of rings 1202, 1204, 1206 to N. Rings 1202, 1204, 1206 to N can be mechanically and electrically isolated into a set of individual elements, and can create planar, focused, or defocused waves. For example, such waves can be centered on-axis, such as by methods of adjusting corresponding transmit and/or receive delays, $\tau_1$, $\tau_2, \tau_3 \ldots \tau_N$. An electronic focus can be suitably moved along various depth positions, and can enable variable strength or beam tightness, while an electronic defocus can have varying amounts of defocusing. In accordance with an exemplary embodiment, a lens can also be provided to aid focusing or defocusing such that any time differential delays can be reduced. Movement of annular array 1200 in one, two or three-dimensions, or along any path, such as through use of probe 1000 and/or robotic arm mechanism 1100, may be implemented to scan and/or treat a volume or any corresponding space within a region of interest.

In accordance with another exemplary embodiment of the present invention, an exemplary variable depth treatment system and method may also be configured to provide therapeutic heating, cooling and/or imaging of a treatment region as well as acoustically monitoring the temperature profile or other tissue parameter monitoring of the treatment region and the general vicinity thereof. In accordance with an exemplary embodiment, an exemplary variable depth system may be configured with a dynamic feedback arrangement based on monitoring of temperature or other tissue parameters, and/or based on imaging information to suitably adjust the spatial and/or temporal characteristics of the variable depth transducer. Such imaging and other temperature or tissue parameter information can be suitably collected from ultrasound signals transmitted from an exemplary variable depth transducer, or from separate devices configured for collecting such information, e.g., a laser device configured with a receiver for profiling temperature, imaging or other such information.

For example, with reference again to FIG. 4, such feedback information can be utilized to dynamically adjust the height, e.g., with a standoff, or distance of a transduction element within variable depth transducer system 402 from superficial layer 412. Such adjustment of the distance and/or location of variable depth transducer system 402 can be controlled either manually or mechanically. Changing the distance of variable depth transducer system 402 can result in a change in the depth of penetration of the acoustical energy within a region of interest, for example, from an inner region 422 to a deep region 410. The depth of penetration of the acoustical energy can also be suitably changed by changing the temperature of any couplant configured between variable depth transducer system 402 from superficial layer 412, and/or the temperature of any coolant.

Feedback information may be suitably generated or provided by any one or more acoustical sources, such as B-scan images, A-lines, Doppler or color flow images, surface acoustic wave devices, hydrophones, elasticity measurement, or shear wave based devices. In addition, optical sources can also be utilized, such as video and/or infrared cameras, laser Doppler imagers, optical coherence tomography imagers, and temperature sensors. Further, feedback information can also be suitably provided by semiconductors, such as thermistors or solid state temperature sensors, by electronic and electromagnetic sensors, such as impedance and capacitance measurement devices and/or thermocouples, and by mechanical sensors, such as stiffness gages, strain gages or stress measurement sensors, or any suitably combination thereof. Moreover, various other switches, acoustic or other sensing mechanisms and methods may be suitably employed to enable transducer 402 to be acoustically coupled to one or more regions of interest.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment with a variable depth transducer as described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, an exemplary variable depth transducer system can also be configured for at least some level of invasive treatment application. These and other changes or modifications are intended to be included within the scope of the present invention, as set forth in the following claims.

The invention claimed is:

1. A non-invasive ultrasound treatment system for providing treatment to a patient, the non-invasive ultrasound treatment system comprising:
   a variable depth transducer comprising a transduction element and a variable depth element, the variable depth transducer operable to provide non-invasive treatment to tissue at least two depths in a patient, the transduction element comprising at least one surface configured to emit acoustic energy, the variable depth element comprising a frequency dependent device configured for spatial control of a focal depth and position of the treatment to the tissue by changing a frequency of the acoustic energy emitted by the at least one surface of the transduction element; and a controller in communication with the variable depth transducer, the controller comprising a control of the spatial control and a control of a frequency range of the acoustic energy.

2. The system according to claim 1, wherein the frequency dependent device is a reflective device.

3. The system according to claim 1, wherein the frequency dependent device is a frequency dependent lens.

4. The system according to claim 1, wherein the frequency dependent device is a frequency dependent mirror device.

5. The system according to claim 1, wherein the frequency dependent device is configured to change a distance from the transduction element to the frequency dependent device, thereby adjust the focal depth of the treatment to the tissue.

6. The according to claim 5, wherein the controller is configured to control the distance from the transduction element to the frequency dependent device.

7. The system according to claim 1, wherein the tissue comprises at least one of a superficial layer and a subcutaneous superficial layer of a patient.

8. The system according to claim 7, wherein the superficial layer includes tissue on or near a surface of the patient.

9. The system according to claim 1, wherein the transduction element is configured to emit acoustic energy at the frequency ranging from about 750 kHz to about 20 MHz.

10. The system according to claim 1, wherein the variable depth transducer is configured for providing at least two of treatment, imaging and temperature monitoring of the tissue.

11. The system according to claim 1, further comprising a coupling system configured for acoustic coupling between the variable depth transducer system and the tissue.

12. The system according to claim 11, wherein the coupling system is configured for temperature control of the variable depth transducer system to facilitate adjustment of the focal depth of the acoustical energy emitted by the at least one surface of the transduction element.

13. The system according to claim 1, wherein the controller further comprises a display unit for displaying at least one of imaging information, positional information, and temperature information of a treatment region comprising the tissue.

14. The system according to claim 1, wherein the controller further comprises a robotic arm arrangement for controlling movement of the variable depth transducer system.

15. An ultrasound system for providing energy deposition at more than one depth, the system comprising:
a variable depth transducer system comprising a transducer and a variable depth element, the variable depth transducer operable to provide energy deposition into tissue comprising at least a deep region and an inner region, the transducer comprising at least one surface configured to emit ultrasound energy at a frequency, the variable depth element comprising a frequency dependent device configured for spatial control of a focal depth of the energy deposition into the tissue by changing the frequency of the ultrasound energy emitted from the at least one surface of the transducer; and
a controller in communication with the transducer and the variable depth element, the controller comprising a control of a frequency range of the ultrasound energy emitted from the at least one surface of the transducer.

16. The system according to claim 15, further comprising a coupling system configured for acoustic coupling between the variable depth transducer system and a region of interest comprising the tissue.

17. The system according to claim 16, wherein the coupling system is configured for temperature control of the transducer to facilitate adjustment of focal depth of the energy deposition into the tissue.

18. The system according to claim 15, wherein the variable depth transducer system is configured to provide the energy deposition into the inner region comprising at least one of a superficial region and a subcutaneous region.

19. The system according to claim 15, further comprising a mechanical scanning device configured to move the variable depth transducer system in at least one of a translational movement and a rotational movement.

20. The system according to claim 15, wherein the at least one surface of the transducer comprises a plurality of transduction elements configured to be activated by a plurality of frequencies separated by at least one phase delay.

21. The system according to claim 15, wherein the energy deposition to the inner region is at a first depth and the energy deposition to the deep treatment region is at a second depth, wherein the first depth is from 0 mm to 5 cm, the second depth is from 50 mm to 7 cm, and the first depth is less than the second depth.

22. The system according to claim 15, wherein the at least one surface of the transducer configured to emit ultrasound energy at the frequency ranging from about 750 kHz to about 20 MHz.

23. The system according to claim 15, wherein the frequency dependent device is a reflective device.

24. The system according to claim 15, wherein the frequency dependent device is a frequency dependent lens.

25. The system according to claim 15, wherein the frequency dependent device is a frequency dependent mirror device.

26. The system according to claim 15, wherein the frequency dependent device is configured to change a distance from the at least one surface of the transducer to the frequency dependent device, thereby adjust the focal depth.

27. The system according to claim 26, wherein the controller is configured to control the distance from the at least one surface of the transducer to the frequency dependent device.

28. The system according to claim 15, wherein the variable depth transducer is configured to provide energy deposition to three different focal depths in the tissue comprising the at least a deep region and an inner region.

29. An ultrasound system for providing energy deposition at more than one depth, the system comprising:
a variable depth transducer system comprising a transducer having at least one surface configured to emit energy to a region of interest at a frequency, and a variable depth element comprising a frequency dependent device configured to simultaneously convert the energy, emitted by the at least one surface of the transducer, into at least three different frequencies and provide energy deposition to at least three different depths in the region of interest; and
a controller in communication with the transducer and the variable depth element, the controller comprising a control of a frequency range of the energy emitted by the at least one surface of the transducer.

\* \* \* \* \*